US008476312B2

(12) United States Patent
Rossi et al.

(10) Patent No.: US 8,476,312 B2
(45) Date of Patent: *Jul. 2, 2013

(54) COMPOSITION COMPRISING (−)-Δ9-TRANS-TETRAHYDROCANNABINOL

(75) Inventors: Ronald Rossi, Mullica Hill, NJ (US); Lee Jonathan Silverberg, Cherry Hill, NJ (US); Robert Hogan, West Grove, PA (US); Ramesh M. Shah, Voorhees, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/596,716

(22) Filed: Aug. 28, 2012

(65) Prior Publication Data

US 2012/0322866 A1 Dec. 20, 2012

Related U.S. Application Data

(60) Continuation of application No. 13/237,388, filed on Sep. 20, 2011, now abandoned, which is a division of application No. 11/595,682, filed on Nov. 10, 2006, now Pat. No. 8,039,509.

(51) Int. Cl.
*A61K 31/35* (2006.01)
(52) U.S. Cl.
USPC .......................................... 514/453; 514/454
(58) Field of Classification Search
USPC ................................. 514/453, 454
See application file for complete search history.

(56) References Cited

U.S. PATENT DOCUMENTS

| | | | |
|---|---|---|---|
| 6,403,126 | B1 | 6/2002 | Webster et al. |
| 7,186,850 | B2 | 3/2007 | Silverberg |
| 7,449,589 | B2 | 11/2008 | Geiser et al. |
| 7,674,922 | B2 | 3/2010 | Burdick et al. |
| 8,039,509 | B2 | 10/2011 | Rossi et al. |
| 8,383,842 | B2 | 2/2013 | Gutman et al. |
| 2004/0229939 | A1 | 11/2004 | Chowdhury et al. |
| 2005/0079136 | A1 | 4/2005 | Woolfe et al. |
| 2006/0160888 | A1 | 7/2006 | Kottayil et al. |
| 2007/0072939 | A1 | 3/2007 | Kupper |
| 2008/0112895 | A1 | 5/2008 | Kottayil et al. |
| 2008/0139644 | A1 | 6/2008 | Rossi et al. |
| 2008/0159961 | A1 | 7/2008 | Woolfe et al. |
| 2009/0181080 | A1 | 7/2009 | Kottayil et al. |

FOREIGN PATENT DOCUMENTS

| | | |
|---|---|---|
| JP | 2006-504671 A | 2/2006 |
| WO | WO-99/32107 A1 | 7/1999 |
| WO | WO-02/096899 A1 | 12/2002 |
| WO | 2004016246 A1 | 2/2004 |
| WO | WO-2006/053766 A1 | 5/2006 |
| WO | WO-2006/063109 A2 | 6/2006 |
| WO | 2008055922 A1 | 5/2008 |
| WO | 2009020666 A1 | 2/2009 |

OTHER PUBLICATIONS

U.S. Appl. No. 60/835,738, by Kottayil et al., filed Aug. 4, 2006.
Turner et al., "Constituents of *Cannabis sativa* L. XVL A Possible Decomposition Pathway of Δ-Tetrahydrocannabinol to Cannabinol," *Journal of Heterocyclic Chemistry*, Dec. 1979, vol. 16, No. 8, pp. 1667-1668.
Munjal et al., "Polymeric Systems for Amorphous Δ$^9$-Tetrahydrocannabinol Produced by a Hot-Melt Method. Part II: Effect of Oxidation Mechanisms and Chemical Interactions and Stability," *Journal of Pharmaceutical Sciences*, Nov. 2006, vol. 95, No. 11, pp. 2473-2485.
Office Action for Japanese Patent Application No. 2009-535748 dated Dec. 11, 2012.
International Search Report dated Jun. 22, 2012 from corresponding PCT Patent Application No. PCT/US2011/061803.
Solvay Pharmaceuticals Inc.: "NDA 18-651/S-021; Marinol (Dronabinol) capsules," Sep. 2004.
Lindholst, "Long term stability of cannabis resin and cannabis extracts," Australian Journal of Forensic Sciences, vol. 42, No. 3, Jul. 2010, pp. 181-190.
Chinese Office Action for Application No. 200780049596.2, dated Apr. 27, 2011.
Provisional Patent U.S. Appl. No. 60/835,738, by Kottayil et al., filed Aug. 4, 2006.
Harvey, "Stability of Cannabinoids in Dried Samples of Cannabis Dating from Around 1896-1905," *Journal of Ethnopharmacology*, 28 (1990) 117-128.
Turner et al., "Constituents of *Cannabis sativa* L. XVL A Possible Decomposition Pathway of Δ-Tetrahydrocannabinol to Cannabinol," *Journal of Heterocyclic Chemistry*, Dec. 1979, vol. 16, No. 8, pp. 1667-1668.
Munjal et al., "Polymeric Systems for Amorphous Δ$^9$-Tetrahydrocannabinol Produced by a Hot-Melt Method. Part II: Effect of Oxidation Mechanisms and Chemical Interactions and Stability," *Journal of Pharmaceutical Sciences*, Nov. 2006, vol. 95, No. 11 pp. 2473-2485.
Dajani et al., "1',1'-Dimethylheptyl-Δ-8-tetrahydrocannabinol-11-oic Acid: A Novel, Orally Effective Cannabinoid with Analgesic and Anti-inflammatory Properties." *JPET* 291: 31-39, 1999.
Thakur et al., "Natural cannabinoids: Templates for drug discovery," *Life Sciences* 78 (2005) 454-466.

*Primary Examiner* — Renee Claytor
(74) *Attorney, Agent, or Firm* — RatnerPrestia

(57) ABSTRACT

A composition comprising a tetrahydrocannabinol compound, a solvent and an acid, wherein the tetrahydrocannabinol compound may be Δ$^8$ tetrahydrocannabinol, (−)-Δ$^9$-trans-tetrahydrocannabinol or a side chain alkyl derivative of either compound, the solvent may be an oil or $C_1$-$C_4$ alcohol (e.g. sesame oil or ethanol), and the acid may be an organic acid or a mineral acid.

20 Claims, 1 Drawing Sheet

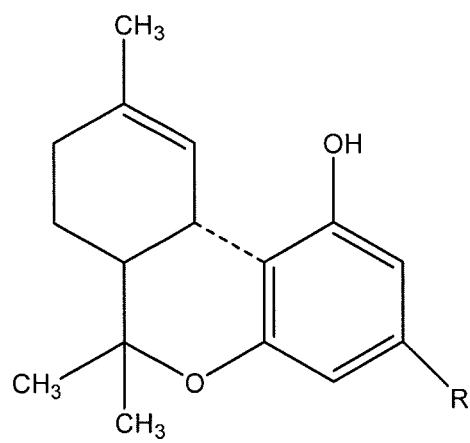
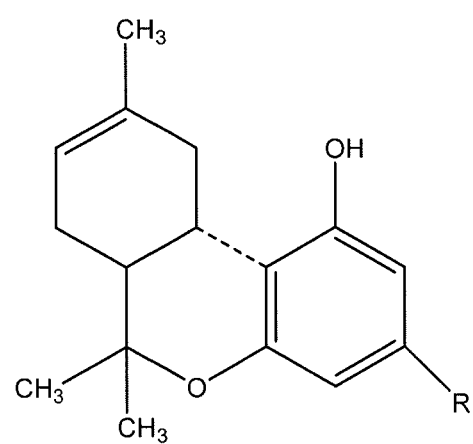

COMPOSITION COMPRISING (−)-Δ9-TRANS-TETRAHYDROCANNABINOL

CROSS-REFERENCE TO RELATED APPLICATIONS

This application is a division of U.S. patent application Ser. No. 13/237,388, filed Sep. 20, 2011, which is a division of U.S. patent application Ser. No. 11/595,682, filed Nov. 10, 2006, the disclosures of both of which are incorporated herein by reference in their entireties for all purposes.

FIELD OF THE INVENTION

The present invention relates to a composition comprising (−)-$\Delta^9$-trans-tetrahydrocannabinol or related compounds.

BACKGROUND OF THE INVENTION

The compound (−)-$\Delta^9$-trans-tetrahydrocannabinol is the active ingredient in marijuana. It is used therapeutically as an inhalant or an oral drug for stimulation of appetite among AIDS and cancer chemotherapy patients. Tetrahydrocannabinols (THCs) can be isolated from marijuana (a mixture of leaves and flowering heads of the plant Cannabis Sativa). Alternatively, THCs can be obtained by synthetic routes, e.g. as described in WO 02/096899.

Pure (−)-$\Delta^9$-trans-tetrahydrocannabinol that has been produced synthetically and purified is unstable and is liable to degrade to products such as cannabinol (which is inactive) and $\Delta^8$-tetrahydrocannabinol (which is less potent). Although $\Delta^8$-tetrahydrocannabinol has similar activity to as (−)-$\Delta^9$-trans-tetrahydrocannabinol it is only approx. 75% as potent and also tends to degrade to other compounds including cannabinol. Dissolving the (−)-$\Delta^9$-trans-tetrahydrocannabinol in a solvent or carrier improves the stability, but it is still usual to store the solutions under refrigerated conditions, e.g. at 5° C., to prevent degradation. The present inventors have sought to improve the stability of solutions of (−)-$\Delta^9$-trans-tetrahydrocannabinol and $\Delta^8$-tetrahydrocannabinol.

SUMMARY OF THE INVENTION

Accordingly, the present invention provides a composition comprising:
 (a) a tetrahydrocannabinol compound chosen from $\Delta^8$ tetrahydrocannabinol, (−)-$\Delta^9$-trans-tetrahydrocannabinol and side chain alkyl derivatives of either compound,
 (b) a solvent chosen from oils and $C_1$-$C_4$ alcohols, and
 (c) an acid.

By side chain alkyl derivatives of either compound we mean compounds with the structure of either of the compounds depicted in the FIGURE, in which R represents an alkyl side chain. Of particular interest, are compounds in which R is 1,1 dimethylheptyl.

BRIEF DESCRIPTION OF THE DRAWINGS

The FIGURE shows the chemical structures for alkyl substituted (−)-$\Delta^8$-trans-tetrahydrocannabinol derivatives and (−)-$\Delta^9$-trans-tetrahydrocannabinol derivatives.

DETAILED DESCRIPTION OF THE INVENTION

The inventors have found that the addition of the acid improves the stability of the composition, i.e. there is less degradation of the tetrahydrocannabinol compound during prolonged storage of the composition.

The composition includes a solvent. The solvent may be chosen from oils and $C_1$-$C_4$ alcohols. Suitable examples of oils include sesame oil, olive oil, canola oil and combinations thereof. Suitable examples of $C_1$-$C_4$ alcohols include methanol, ethanol, propanol, iso-propanol and butanol.

According to one embodiment, the solvent is sesame oil. The sesame oil may be refined or unrefined, but is preferably refined (the US Food and Drug Administration standards require that refined sesame oil is used in pharmaceutical products). The composition may further comprise other solvents, but preferably comprises only sesame oil as the solvent. According to an alternative embodiment, the solvent is ethanol.

The acid used in the composition may be an organic acid. When an organic acid is used, the organic acid is suitably chosen from citric acid, ascorbic acid, malic acid, oxalic acid, succinic acid and tartaric acid, and is preferably citric acid.

The acid used in the composition may be a mineral acid. When a mineral acid is used, the mineral acid is suitably chosen from phosphoric acid, hydrochloric acid, nitric acid and sulphuric acid, and is preferably phosphoric acid.

Weak acids have an especially positive stabilizing effect on (−)-$\Delta^9$-trans-tetrahydrocannabinol and its derivatives, forming a stabilized composition. If the amount or concentration of strong acid is too large, the $\Delta^9$-isomer degrades to the $\Delta^8$-isomer.

The acid may be added to the other constituents either as a separate component, or the acid may be formed in a solution of the other constituents. An example of the latter is the use of dissolved $CO_2$ in ethanol, which also stabilizes the $\Delta^9$-isomer, probably due to formation of carbonic acid.

The amount of acid is suitably from 0.01-2% as a weight percentage of the composition, preferably from 0.02-1% and most preferably from 0.05-0.5%.

The amount of (−)-$\Delta^9$-trans-tetrahydrocannabinol in the composition is suitably from 0.1-15% as a weight percentage of the composition, preferably from 1 to 10%.

The composition may further comprise antimicrobial agents such as methyl paraben or propyl paraben. The composition may further comprise preservatives such as alpha-tocopherol or butylated hydroxytoluene (BHT). The composition may further comprise antioxidants. The antimicrobial agents, preservatives and antioxidants may be used alone or in combination.

In a preferred embodiment, the composition of the invention consists essentially of a tetrahydrocannabinol compound, an oil or a $C_1$-$C_4$ alcohol, and 0.01-2 wt % of an acid chosen from the group consisting of citric acid, ascorbic acid, malic acid, oxalic acid, succinic acid, tartaric acid, phosphoric acid, hydrochloric acid, nitric acid and sulphuric acid. Additional components (e.g. antimicrobial agents, preservatives, antioxidants) may comprise up to 1 wt % of the solution. In an especially preferred embodiment, the composition of the invention consists essentially of (−)-$\Delta^9$-trans-tetrahydrocannabinol, sesame oil and 0.05-0.5 wt % citric acid or phosphoric acid, wherein additional components may comprise up to 1 wt % of the solution.

Compositions according to the invention may be prepared by adding the acid to a solution of a tetrahydrocannabinol compound in sesame oil or a $C_1$-$C_4$ alcohol and mixing. Solutions of (−)-$\Delta^9$-trans-tetrahydrocannabinol in sesame oil may be prepared by dissolving pure (−)-$\Delta^9$-trans-tetrahydrocannabinol in sesame oil, or by mixing sesame oil with a solution of (−)-$\Delta^9$-trans-tetrahydrocannabinol in ethanol, and then distilling off the ethanol.

The following examples are illustrative but not limiting of the invention.

Composition Preparation: Sesame Oil Solvent

Sesame oil was degassed under vacuum distillation and blanketed with nitrogen. The sesame oil was refined sesame oil from Jeen International (Compositions 1-2, 7-17) or Dipasa (Compositions 3-6). A solution of (−)-$\Delta^9$-trans-tetrahydrocannabinol in ethanol was added to the sesame oil and the acid was also added. The solution was mixed and the ethanol was removed using a rotary evaporator.

Each composition contained 6.65 wt % (−)-$\Delta^9$-trans-tetrahydrocannabinol based on the weight of the composition. The additional components in each composition were as shown in Table 1 below:

TABLE 1

Compositions 1-18 in Sesame Oil Solvent

| | Acid | Other components |
|---|---|---|
| Composition 1 | None | None |
| Composition 2 | 0.1 wt % citric acid | None |
| Composition 3 | None | None |
| Composition 4 | 0.1 wt % citric acid | None |
| Composition 5 | None | Methyl paraben, Propyl paraben, Alpha tocopherol, BHT |
| Composition 6 | 0.1 wt % citric acid | Methyl paraben, Propyl paraben, Alpha tocopherol, BHT |
| Composition 7 | None | None |
| Composition 8 | 0.1 wt % ascorbic acid | None |
| Composition 9 | 0.1 wt % acetic acid | None |
| Composition 10 | 0.1 wt % citric acid | None |
| Composition 11 | 0.1 wt % lactic acid | None |
| Composition 12 | 0.1 wt % fumaric acid | None |
| Composition 13 | 0.1 wt % malic acid | None |
| Composition 14 | 0.1 wt % oxalic acid | None |
| Composition 15 | 0.1 wt % succinic acid | None |
| Composition 16 | 0.1 wt % salicylic acid | None |
| Composition 17 | 0.1 wt % tartaric acid | None |
| Composition 18 | 0.1 wt % phosphoric acid | None |

Composition Preparation: Ethanol Solvent

Citric acid was added to 2 ml samples of a solution of (−)-$\Delta^9$-trans-tetrahydrocannabinol in ethanol (the concentration of the (−)-$\Delta^9$-trans-tetrahydrocannabinol was 66.6 mg/ml). The solutions were mixed. The amount of citric acid in each solution is shown in Table 2 below:

TABLE 2

Compositions 19-24 in Ethanol Solvent

| | Amount of citric acid (mg) | Weight % of citric acid compared to the weight of $\Delta^9$-THC |
|---|---|---|
| Composition 19 | 0.00 | 0.0% |
| Composition 20 | 2.51 | 1.9% |
| Composition 21 | 2.01 | 1.5% |
| Composition 22 | 0.50 | 0.4% |
| Composition 23 | 0.25 | 0.2% |
| Composition 24 | 0.13 | 0.09% |

Stability: Sesame Oil Solvent

The stability of the sesame oil compositions (compositions 1-18) was assessed at three different conditions: 5° C. or Normal Storage (Refrigerated) Conditions; 25° C./60% Relative Humidity or Accelerated Conditions; and 40° C./75% Relative Humidity or High Temperature/High Humidity Conditions. The degradation of the (−)-$\Delta^9$-trans-tetrahydrocannabinol was monitored using a High Performance Liquid Chromatography (HPLC) method with ultraviolet detection at 228 nm. Each detected impurity peak was measured using percent peak area (% PA) with respect to the peak area counts for (−)-$\Delta^9$-trans-tetrahydrocannabinol for each chromatogram. Each impurity peak was identified with a relative retention time (RRT) relative to the (−)-$\Delta^9$-trans-tetrahydrocannabinol peak elution time from each chromatogram. Impurity peaks measuring above 0.05% PA were recorded.

The impurities that are attributed to the degradation of (−)-$\Delta^9$-trans-tetrahydrocannabinol elute from the HPLC column at a RRT window of 0.56 to 0.95 and at a RRT of 1.06. The impurities cannabinol and $\Delta^8$-tetrahydrocannabinol elute from the column at RRTs of 0.95 and 1.06 respectively.

Table 3 shows the results of the stability tests for compositions 1-18. The period of time after which the degradation of the composition was assessed is indicated beside each table.

TABLE 3

Stability tests for compositions 1-18

| | % Peak Areas according to Relative Retention Time (RRT) | | | | | | | | | | | | |
|---|---|---|---|---|---|---|---|---|---|---|---|---|---|
| Condition | 0.56 | 0.57 | 0.58 | 0.61 | 0.63 | 0.66 | 0.67 | 0.70 | 0.74 | 0.78 | 0.90 | 0.95 | 1.06 |
| Composition 1, 1 month | | | | | | | | | | | | | |
| Initial | | | | | | | | | | | | | 0.28 |
| 25° C./60% RH | | 4.13 | 4.45 | 0.96 | 3.11 | 10.2 | 2.35 | 0.22 | | 0.36 | 1.46 | 4.06 | 5.33 |
| 40° C./75% RH | | 8.09 | 5.35 | 2.43 | 4.91 | 0.29 | 15.62 | 0.28 | | | 0.49 | 1.86 | 2.99 |
| Composition 2, 3 months | | | | | | | | | | | | | |
| Initial | | | | | | | | | | | | | |
| 5° C. | | | 0.08 | 0.05 | | | | | | | | 0.05 | |
| 25° C./60% RH | 0.18 | | | 0.13 | | 0.07 | | 0.07 | | | 0.16 | 0.37 | 0.29 |
| 40° C./75% RH | 1.96 | | 0.22 | 0.91 | 0.17 | 0.45 | 0.36 | 0.3 | | 0.05 | 1.25 | 4.16 | 2.17 |
| Composition 3, 3 months | | | | | | | | | | | | | |
| Initial | | | | | 0.12 | | | | | | | | |
| 5° C. | 0.29 | 0.51 | | 0.29 | 0.13 | 3.96 | 0.22 | | 0.35 | 1.89 | | 0.15 | 0.08 |
| 25° C./60% RH | 0.85 | 0.74 | 1.97 | 1.23 | 0.72 | 6.13 | 1.81 | 0.06 | 0.23 | 2.55 | 0.44 | 2.03 | 0.64 |
| 40° C./75% RH | 0.16 | 0.52 | 0.31 | 0.65 | 0.74 | 3.72 | 0.45 | 0.02 | 0.08 | 1.02 | 1.96 | 1.46 | 0.7 |

TABLE 3-continued

Stability tests for compositions 1-18

% Peak Areas according to Relative Retention Time (RRT)

| Condition | 0.56 | 0.57 | 0.58 | 0.61 | 0.63 | 0.66 | 0.67 | 0.70 | 0.74 | 0.78 | 0.90 | 0.95 | 1.06 |
|---|---|---|---|---|---|---|---|---|---|---|---|---|---|
| *Composition 4, 3 months* | | | | | | | | | | | | | |
| Initial | | | | | | | | | | | | | |
| 5° C. | | | | | | | | | | | | 0.05 | |
| 25° C./60% RH | 0.19 | | | 0.10 | | | | | | | 0.10 | 0.20 | 0.14 |
| 40° C./75% RH | 1.96 | | | 0.15 | 0.53 | 0.29 | 0.30 | 0.17 | | | 1.11 | 2.62 | 0.41 |
| *Composition 5, 3 months* | | | | | | | | | | | | | |
| Initial | | | | | | | | | 1.54 | | | | |
| 5° C. | 0.05 | 0.12 | | | 0.08 | 0.06 | | | 1.36 | 0.05 | 0.09 | | 0.30 |
| 25° C./60% RH | 0.40 | 0.65 | 0.2 | 0.13 | 0.41 | 0.50 | 0.37 | 0.14 | 0.92 | 0.12 | 0.27 | 0.48 | 1.00 |
| 40° C./75% RH | 1.05 | 0.63 | 0.23 | 0.11 | 0.91 | 0.62 | 0.22 | | 1.07 | 0.11 | 0.54 | 1.63 | 1.74 |
| *Composition 6, 3 months* | | | | | | | | | | | | | |
| Initial | | | | 0.05 | | | | | 1.54 | | | | |
| RF 5° C. | | | | 0.06 | | | | | 1.52 | | | 0.11 | 0.05 |
| 25° C./60% RH | 0.09 | | | 0.06 | | 0.07 | | | 1.52 | | | 0.53 | 0.3 |
| 40° C./75% RH | 0.97 | 0.21 | 0.15 | 0.52 | 0.25 | 0.32 | 0.2 | 0.18 | 1.57 | | 0.63 | 2.96 | 1.96 |
| *Composition 7, 4 weeks* | | | | | | | | | | | | | |
| Initial | | 0.03 | 0.03 | | | 0.02 | | | | 0.01 | | | 0.02 |
| 5° C. | 0.01 | | | | | 0.11 | 0.02 | | 0.04 | 0.04 | 0.01 | | 0.05 |
| 25° C./60% RH | 0.19 | 0.16 | | 0.13 | 0.11 | 1.76 | | | 0.51 | 0.22 | 0.01 | 0.05 | 0.05 |
| 40° C./75% RH | 0.23 | 0.21 | 0.46 | 1.41 | 0.67 | 5.60 | 0.22 | 0.07 | 1.00 | 0.81 | 0.29 | 0.56 | 0.05 |
| *Composition 8, 4 weeks* | | | | | | | | | | | | | |
| Initial | 0.01 | | 0.01 | | 0.01 | | | | | 0.01 | | | 0.02 |
| 5° C. | | | 0.02 | | | | | | | 0.01 | | | 0.02 |
| 25° C./60% RH | | | 0.03 | 0.03 | | | | | | | 0.02 | 0.01 | 0.02 |
| 40° C./75% RH | 0.02 | 0.01 | 0.06 | 0.11 | 0.03 | | | | 0.02 | 0.02 | 0.04 | 0.05 | 0.06 |
| *Composition 9, 4 weeks* | | | | | | | | | | | | | |
| Initial | 0.02 | | | | | 0.04 | 0.03 | | | | | | 0.02 |
| 5° C. | 0.17 | 0.10 | 0.02 | 0.1 | 0.02 | 0.67 | 0.16 | | 0.15 | 0.15 | | 0.02 | 0.05 |
| 25° C./60% RH | 0.13 | 0.23 | 0.36 | 1.00 | 0.09 | 3.18 | 0.46 | 0.02 | 0.58 | 0.59 | 0.1 | 0.68 | 0.14 |
| 40° C./75% RH | 0.65 | 1.25 | 0.29 | 2.95 | 0.32 | 2.99 | 1.71 | 0.04 | 0.30 | 0.12 | 0.49 | 3.69 | 0.7 |
| *Composition 10, 4 weeks* | | | | | | | | | | | | | |
| Initial | 0.02 | | | | | | 0.01 | | | | | 0.01 | 0.02 |
| 5° C. | | | | | | | | | | | 0.01 | | 0.01 |
| 25° C./60% RH | | | 0.04 | | | | | | | | 0.03 | 0.01 | 0.02 |
| 40° C./75% RH | 0.11 | | 0.11 | 0.02 | 0.02 | 0.02 | 0.02 | 0.03 | | | 0.16 | 0.12 | 0.14 |
| *Composition 11, 4 weeks* | | | | | | | | | | | | | |
| Initial | | | 0.02 | | | | | | | | | | 0.02 |
| 5° C. | | | 0.02 | | | | | | | 0.01 | 0.02 | 0.02 | 0.03 |
| 25° C./60% RH | 0.02 | 0.01 | 0.09 | | 0.01 | | | | | | 0.04 | 0.11 | 0.07 |
| 40° C./75% RH | 0.02 | 0.19 | 0.12 | 0.27 | 0.04 | 0.16 | 0.04 | | | 0.02 | 0.33 | 0.60 | 0.43 |
| *Composition 12, 4 weeks* | | | | | | | | | | | | | |
| Initial | 0.02 | | 0.01 | | 0.02 | | | | 0.03 | | | | 0.01 |
| 5° C. | 0.26 | 0.10 | 0.09 | | 0.05 | 0.42 | 0.17 | | 0.09 | 0.12 | 0.01 | 0.02 | 0.06 |
| 25° C./60% RH | 0.08 | 0.09 | 0.12 | 0.02 | 0.07 | 0.38 | 0.1 | 0.02 | 0.04 | 0.07 | 0.19 | 0.19 | 0.67 |
| 40° C./75% RH | 0.42 | 0.11 | 0.53 | 0.07 | 0.16 | 0.31 | 0.32 | | 0.07 | 0.04 | 0.98 | 1.41 | 2.58 |
| *Composition 13, 4 weeks* | | | | | | | | | | | | | |
| Initial | | | | | | | | | | | | | 0.02 |
| 5° C. | | | | | | | | | | | 0.01 | | 0.01 |
| 25° C./60% RH | 0.01 | | 0.02 | | | | | | | | 0.02 | 0.03 | 0.03 |
| 40° C./75% RH | 0.15 | | 0.02 | 0.06 | 0.04 | 0.03 | | 0.03 | | | 0.15 | 0.18 | 0.18 |
| *Composition 14, 4 weeks* | | | | | | | | | | | | | |
| Initial | 0.01 | | | | | | | | | | | | 0.02 |
| 5° C. | | | 0.05 | | | | | | | | 0.01 | | 0.02 |
| 25° C./60% RH | | | 0.16 | | | | | | | | 0.03 | 0.03 | 0.02 |
| 40° C./75% RH | 0.04 | 0.03 | 0.35 | 0.02 | | | | | | | 0.11 | 0.12 | 0.02 |
| *Composition 15, 4 weeks* | | | | | | | | | | | | | |
| Initial | | | | | 0.02 | | | | 0.02 | | 0.01 | | 0.02 |
| 5° C. | | | | | | | | | | | 0.01 | 0.01 | 0.02 |
| 25° C./60% RH | | | 0.03 | | 0.02 | | | | | | 0.01 | | 0.03 |
| 40° C./75% RH | 0.05 | 0.01 | 0.25 | 0.03 | 0.08 | 0.08 | 0.03 | | 0.03 | | 0.11 | 0.10 | 0.28 |

TABLE 3-continued

Stability tests for compositions 1-18

% Peak Areas according to Relative Retention Time (RRT)

| Condition | 0.56 | 0.57 | 0.58 | 0.61 | 0.63 | 0.66 | 0.67 | 0.70 | 0.74 | 0.78 | 0.90 | 0.95 | 1.06 |
|---|---|---|---|---|---|---|---|---|---|---|---|---|---|
| Composition 16, 4 weeks | | | | | | | | | | | | | |
| Initial | 0.01 | | 0.04 | | 0.01 | 0.01 | 0.02 | | | | | 0.01 | 0.03 |
| 5° C. | 0.01 | | 0.16 | | 0.03 | 0.08 | 0.04 | | 0.05 | 0.15 | 0.01 | 0.22 | 0.07 |
| 25° C./60% RH | 0.36 | 0.1 | 1.87 | | 0.58 | 0.63 | 0.75 | 0.01 | 0.19 | 2.76 | 0.05 | 4.27 | 0.15 |
| 40° C./75% RH | 0.41 | 0.27 | 0.99 | 0.17 | 0.45 | 0.34 | 0.77 | 0.05 | 0.08 | 2.97 | 0.64 | 4.5 | 0.59 |
| Composition 17, 4 weeks | | | | | | | | | | | | | |
| Initial | 0.02 | | | | | | 0.01 | | | 0.02 | | | 0.02 |
| 5° C. | | | | | | | | | | | 0.01 | | 0.02 |
| 25° C./60% RH | | | 0.02 | | | | | | | 0.02 | | 0.02 | 0.02 |
| 40° C./75% RH | 0.13 | | 0.04 | 0.04 | 0.01 | 0.04 | | 0.03 | | | 0.12 | 0.12 | 0.17 |
| Composition 18, 16 days | | | | | | | | | | | | | |
| Initial | | | 1.58 | 0.26 | 0.55 | | | | 0.36 | | 0.05 | | |
| 25° C./60% RH | | | 3.39 | 0.20 | 0.17* | 0.09 | | | | 0.09 | | 1.08 | |
| 40° C./75% RH | | | 3.39 | 0.20 | 0.18* | 0.08 | | | 0.10 | | | 1.08 | | data after 1 week, not 16 days

Compositions 1, 3, 5 and 7 did not contain any organic acid, and the tables show that considerable degradation occurred during the observation period. By contrast, the degradation observed for compositions 2, 4 and 6 (which all contained 0.1 wt % citric acid) was considerably less. Compositions 5 and 6 both contained antimicrobial agents and preservatives, yet composition 6 (containing 0.1 wt % citric acid) was more stable than composition 5.

Compositions 8-18 contained a variety of acids. Compositions 8, 10, 11, 12, 13, 14, 15, 17 and 18 (containing 0.1 wt % ascorbic acid, 0.1 wt % citric acid, 0.1 wt % lactic acid, 0.1 wt % fumaric acid, 0.1 wt % malic acid, 0.1 wt % oxalic acid, 0.1 wt % succinic acid, 0.1 wt % tartaric acid and 0.1 wt % phosphoric acid respectively) all showed improved stability compared to composition 7 (containing no organic acid). Compositions 9 and 16 (containing 0.1 wt % acetic acid and 0.1 wt % salicylic acid) did not show an appreciable improvement compared to composition 7 and it would seem that these acids are less effective at improving stability (although the inventors believe that these acid may provide an improvement if used at another concentration).

Stability: Ethanol Solvent

The stability of the ethanol compositions (compositions 19-24) was assessed in substantially the same manner as for the sesame oil compositions except that they were only assessed at only one set of conditions (40° C.) and the compositions were analysed after 60 hours and 1 month.

Table 4 shows that the composition that did not contain citric acid (composition 19) showed the greatest degradation and there seems to be a slight correlation between increasing citric acid content and increased stability.

TABLE 4

Stability tests for compositions 19-24

% Peak Areas according to Relative Retention Time (RRT)

| | Condition | 0.57 | 0.58 | 0.59 | 0.61 | 0.63 | 0.66 | 0.67 | 0.70 | 0.74 | 0.78 | 0.82 | 0.90 | 0.95 |
|---|---|---|---|---|---|---|---|---|---|---|---|---|---|---|
| | Initial | | | | | | 0.11 | | | | | | | |
| Composition 19 | 40° C./60 hr | 0.04 | 0.04 | | 0.25 | 0.02 | 1.80 | | | 0.35 | | 0.02 | | 0.34 |
| | 40° C./1 mo | 0.34 | 0.34 | 0.14 | 8.6 | 1.58 | 5.13 | | 0.13 | 2.33 | 0.07 | 1.46 | 0.52 | 0.34 |
| Composition 20 | 40° C./60 hr | | | | 0.3 | 0.02 | | | | | | 0.04 | | 0.07 |
| | 40° C./1 mo | 0.02 | | | 2.38 | 0.19 | 0.03 | 0.06 | 0.02 | | | 0.05 | 0.01 | 0.58 |
| Composition 21 | 40° C./60 hr | 0.04 | | | 0.3 | 0.02 | 0.01 | | | | | 0.05 | | 0.08 |
| | 40° C./1 mo | 0.02 | | | 2.51 | 0.2 | 0.02 | 0.06 | 0.02 | | | 0.05 | 0.01 | 0.6 |
| Composition 22 | 40° C./60 hr | | | | 0.35 | 0.03 | 0.07 | | | | | 0.11 | | 0.04 |
| | 40° C./1 mo | 0.02 | | | 3.37 | 0.27 | 0.06 | 0.06 | 0.03 | | | 0.23 | 0.02 | 0.69 |
| Composition 23 | 40° C./60 hr | | | | 0.31 | 0.03 | 0.11 | | | | | 0.11 | | 0.02 |
| | 40° C./1 mo | 0.02 | 0.02 | | 3.03 | 0.25 | 0.12 | 0.04 | 0.03 | | | 0.42 | 0.01 | 0.51 |
| Composition 24 | 40° C./60 hr | 0.02 | | | 0.28 | 0.03 | 0.16 | | | 0.02 | | 0.11 | | 0.02 |
| | 40° C./1 mo | 0.02 | | | 1.71 | 0.14 | 0.13 | 0.02 | 0.03 | | | 0.39 | | 0.24 |

The invention claimed is:

1. A composition comprising:
(a) a tetrahydrocannabinol compound selected from $\Delta^8$ tetrahydrocannabinol, $(-)$-$\Delta^9$-trans-tetrahydrocannabinol and side chain alkyl derivatives of either compound,
(b) a solvent comprising ethanol, and
(c) carbonic acid.

2. A composition consisting essentially of:
a) a tetrahydrocannabinol compound selected from $\Delta^8$-tetrahydrocannabinol, $(-)$-$\Delta^9$-trans-tetrahydrocannabinol and side chain alkyl derivatives of either compound,
b) a solvent comprising ethanol, and
c) carbonic acid, and, optionally, one or more anti-oxidants, antimicrobial agents, preservatives or a combination thereof.

3. A composition according to claim 1, wherein the carbonic acid is formed from dissolved $CO_2$ in the ethanol.

4. A composition according to claim 2, wherein the carbonic acid is formed from dissolved $CO_2$ in the ethanol.

5. A composition according to claim 1 further comprising one or more anti-oxidants, antimicrobial agents, preservatives or a combination thereof.

6. A composition according to claim 2, wherein the composition includes the one or more anti-oxidants, antimicrobial agents, preservatives or a combination thereof.

7. A composition according to claim 1 further comprising alpha-tocopherol.

8. A composition according to claim 1 further comprising butylated hydroxytoluene.

9. A composition according to claim 1, wherein the carbonic acid is present in an amount of from 0.01-2 wt. %.

10. A composition according to claim 2, wherein the carbonic acid is present in an amount of from 0.01-2 wt. %.

11. A composition according to claim 1, wherein the carbonic acid is present in an amount of from 0.02-1 wt. %.

12. A composition according to claim 2, wherein the carbonic acid is present in an amount of from 0.02-1 wt. %.

13. A composition according to claim 1, wherein the carbonic acid is present in an amount of from 0.05-0.5 wt. %.

14. A composition according to claim 2, wherein the carbonic acid is present in an amount of from 0.05-0.5 wt. %.

15. A composition according to claim 1, wherein the tetrahydrocannabinol compound is (-)-$\Delta^9$-trans-tetrahydrocannabinol.

16. A composition according to claim 2, wherein the tetrahydrocannabinol compound is (-)-$\Delta^9$-trans-tetrahydrocannabinol.

17. A composition according to claim 15, wherein the (-)-$\Delta^9$-trans-tetrahydrocannabinol is present in an amount from 0.1-15 wt. %.

18. A composition according to claim 16 wherein the (-)-$\Delta^9$-trans-tetrahydrocannabinol is present in an amount from 0.1-15 wt. %.

19. A composition according to claim 15, wherein the (-)-$\Delta^9$-trans-tetrahydrocannabinol is present in an amount from 1-10 wt. %.

20. A composition according to claim 16 wherein the (-)-$\Delta^9$-trans-tetrahydrocannabinol is present in an amount from 1-10 wt. %.

* * * * *